United States Patent
Chen et al.

(10) Patent No.: US 12,025,604 B2
(45) Date of Patent: Jul. 2, 2024

(54) TRANSFER AND ONLINE DETECTION SYSTEM FOR DEEP-SEA SEDIMENT SAMPLES AND APPLICATION METHOD THEREOF

(71) Applicants: Zhejiang University, Zhejiang (CN); Guangzhou Marine Geological Survey, Guangdong (CN); Dalian University of Technology, Liaoning (CN); Hangzhou Dianzi University, Zhejiang (CN)

(72) Inventors: Jiawang Chen, Zhejiang (CN); Bo Xiao, Zhejiang (CN); Qiaoling Gao, Zhejiang (CN); Jiafei Zhao, Zhejiang (CN); Qinghua Sheng, Zhejiang (CN)

(73) Assignees: ZHEJIANG UNIVERSITY, Zhoushan (CN); GUANGZHOU MARINE GEOLOGICAL SURVEY, Guangzhou (CN); DALIAN UNIVERSITY OF TECHNOLOGY, Dalian (CN); HANGZHOU DIANZI UNIVERSITY, Hangzhou (CN)

( * ) Notice: Subject to any disclaimer, the term of this patent is extended or adjusted under 35 U.S.C. 154(b) by 366 days.

(21) Appl. No.: 17/551,695

(22) Filed: Dec. 15, 2021

(65) Prior Publication Data
US 2022/0187271 A1 Jun. 16, 2022

Related U.S. Application Data

(63) Continuation-in-part of application No. PCT/CN2021/117457, filed on Sep. 9, 2021.

(30) Foreign Application Priority Data

Dec. 15, 2020 (CN) .......................... 202011476358.3

(51) Int. Cl.
*G01N 33/24* (2006.01)
*E21B 25/18* (2006.01)
(Continued)

(52) U.S. Cl.
CPC .............. *G01N 33/24* (2013.01); *E21B 25/18* (2013.01); *G01N 1/286* (2013.01); *G01N 1/42* (2013.01); *G01N 2001/2873* (2013.01)

(58) Field of Classification Search
CPC .......... G01N 33/24; G01N 1/286; G01N 1/42; G01N 2001/2873; G01N 2001/1006; G01N 2001/1062; G01N 1/10; E21B 25/18
See application file for complete search history.

(56) References Cited

U.S. PATENT DOCUMENTS 4,317,490 A * 3/1982 Milberger ............... E21B 25/08
175/20

FOREIGN PATENT DOCUMENTS

CN 103913356 A 7/2014
CN 104364566 A * 2/2015 ............. F16H 61/28
(Continued)

*Primary Examiner* — Tarun Sinha
*Assistant Examiner* — Drexel Alejandro Venero
(74) *Attorney, Agent, or Firm* — HoustonHogle LLP

(57) ABSTRACT

A transfer and online detection system for deep-sea sediment samples and an application method thereof are provided. A sample gripping and feeding device, a sample segment cutting device, a sample online detection device, a high-pressure ball valve and a pressure-retaining drill disengaging device of the system are coaxially connected with one another. A seawater booster pump is connected with a water inlet ball valve, and a valve control panel is connected with the sample gripping and feeding device, the sample segment cutting device, the high-pressure ball valve and the pressure-retaining drill disengaging device. The pressure-retaining drill disengaging device is configured for disengaging an (Continued)

inner barrel and an inner barrel joint, and the sample gripping and feeding device and the sample segment cutting device are configured for gripping and cutting core samples, and conveying the cut core samples into a subsample pressure-retaining storage cylinder for storage.

6 Claims, 6 Drawing Sheets

(51) Int. Cl.
*G01N 1/28* (2006.01)
*G01N 1/42* (2006.01)

(56) References Cited

FOREIGN PATENT DOCUMENTS

| | | | |
|---|---|---|---|
| CN | 106950355 A | | 7/2017 |
| CN | 109030076 A | | 12/2018 |
| CN | 208223844 U | | 12/2018 |
| CN | 109187122 A | | 1/2019 |
| CN | 109262698 A | | 1/2019 |
| CN | 109958401 A | | 7/2019 |
| CN | 110726581 A | | 1/2020 |
| CN | 110823799 A | * | 2/2020 |
| CN | 211851650 U | * | 11/2020 |
| JP | 2017129577 A | | 7/2017 |
| KR | 20140069688 A | | 6/2014 |

\* cited by examiner

TRANSFER AND ONLINE DETECTION SYSTEM FOR DEEP-SEA SEDIMENT SAMPLES AND APPLICATION METHOD THEREOF

CROSS REFERENCE TO RELATED APPLICATION

This application claims priority to Chinese Patent Application No. 202011476358.3, filed on Dec. 15, 2020 and is also a Continuation-in-Part of International Patent Application No. PCT/CN2021/117457, filed on Sep. 9, 2021, which designates the United States, and which International Application, in turn, claims priority to Chinese Patent Application No. 202011476358.3, filed on Dec. 15, 2020, all of which are incorporated herein by reference in their entirety.

TECHNICAL FIELD

The present disclosure relates to the field of deep-sea seabed resource detection and investigation techniques and related equipment development, and in particular to a transfer and online detection system for deep-sea sediment samples and an application method thereof.

BACKGROUND ART

There are diversified resources in seabeds, including polymetallic nodules, cobalt crust, hydrothermal sulfide, marine organisms, petroleum, natural gas, natural gas hydrate and clay minerals, which are of great economic value. It is necessary to have a good understanding of the oceans before development and utilization of such resources. For this purpose, marine geologic survey should be carried out to grasp the type, distribution, mineralization condition, resource prospect and other basic information of relevant resources.

Sampling deep-sea sediments is considered as one of the important technical means to conduct marine geologic survey. At present, the technology of seabed sediment pressure-retaining sampling has been well developed around the globe. It can help extract sediments from the seabed to the sea surface while maintaining the in-situ pressure of the sediments, and acquire minimum disturbed samples of seabed sediments. However, fewer studies have been made on how to cut acquired samples into random segments while maintaining the in-situ pressure, and store and convey the sample segments to a laboratory under retained pressure to better study physical properties of sediments.

SUMMARY

The objective of the present embodiment is to provide a transfer and online detection system for deep-sea sediment samples and an application method thereof to resolve the foregoing problems in the prior art. In this way, acquired samples may be cut into random segments while the in-situ pressure is maintained, and are stored and conveyed to a laboratory under retained pressure to better study physical properties of sediments.

To achieve the foregoing objective, the present disclosure provides the following solution:

The present disclosure provides transfer and online detection system for deep-sea sediment samples, comprising a sample gripping and feeding device, a sample segment cutting device, a high-pressure ball valve, a pressure-retaining drill disengaging device, a subsample pressure-retaining storage cylinder, a cool water tank, an online sample detection device, a monitoring and operating system, and a seawater cooling and pressurizing system, wherein the sample gripping and feeding device, the sample segment cutting device, the online sample detection device, the high-pressure ball valve and the pressure-retaining drill disengaging device are coaxially connected together in sequence; a seawater booster pump in the seawater cooling and pressurizing system is connected with a water inlet main ball valve in a valve control panel through a pipeline, and the valve control panel is connected with the sample gripping and feeding device, the sample segment cutting device, the high-pressure ball valve and the pressure-retaining drill disengaging device through branches and valves on the branches; and the cool water tank is configured for cooling a sampling drill, the pressure-retaining drill disengaging device is configured for disengaging an inner barrel from an inner barrel joint of the sampling drill, and the sample gripping and feeding device and the sample segment cutting device are configured for gripping and cutting core samples, and conveying the core samples cut into the subsample pressure-retaining storage cylinder for storage.

In some embodiments, the sample gripping and feeding device may include a first motor, a first hoop, a front pressure-retaining cylinder segment, a second hoop, a rear pressure-retaining cylinder segment, a third hoop, a rear end cover, a lead screw, a guide rail, a gripper, an auxiliary supporting slide block, a gripping rod, a gears joint, a driving slide block and a front end cover. The front pressure-retaining cylinder segment and the front end cover may be coaxially connected via the first hoop, the front pressure-retaining cylinder segment and the rear pressure-retaining cylinder segment may be coaxially connected via the second hoop, and the rear pressure-retaining cylinder segment and the rear end cover may be coaxially connected via the third hoop. The guide rail may be arranged in the front pressure-retaining cylinder segment and the rear pressure-retaining cylinder segment via screws and configured for guiding the auxiliary supporting slide block and the driving slide block to axially move. The auxiliary supporting slide block and the driving slide block each may be arranged on the guide rail and coaxial with the front pressure-retaining cylinder segment and may form a gap with an inner wall of the front pressure-retaining cylinder segment. Two ends of the lead screw may be arranged to the front end cover and the rear end cover respectively, the lead screw may penetrate through through holes in the driving slide block and the auxiliary supporting slide block, the gears joint may be arranged on the lead screw, one end of the gripping rod may be fixedly connected with the gears joint, another end of the gripping rod may be provided with the gripper, and the gears joint is capable of converting rotational movement of the lead screw into axial translational movement of the gripping rod. The first motor may be connected with one end of the lead screw via a first coupler and may be configured to drive the lead screw to rotate.

In some embodiments, the sample segment cutting device may include a cabin, a right end cover, a second motor, a clamping handwheel, a left end cover, a third motor, a first worm-and-gear pair, a second worm-and-gear pair, a third worm-and-gear pair, three cutters, a first spiral slotted disc, three first clamps and a second spiral slotted disc. The right end cover and the left end cover may be coaxially connected to the cabin via bolts. A worm gear of the first worm-and-gear pair, a worm gear of the third worm-and-gear pair, the first spiral slotted disc and the second spiral slotted disc may be coaxially arranged in the cabin, the worm gear of the first worm-and-gear pair may be coaxially connected to the second spiral slotted disc via bolts, and the worm gear of the third worm-and-gear pair may be coaxially connected to the first spiral slotted disc via bolts. The three cutters may be arranged on the first spiral slotted disc at an interval of 120 degrees, and may be controlled to advance or retreat by forward and reverse rotations of the first spiral slotted disc. The first clamps may be arranged on the second spiral slotted disc at an interval of 120 degrees, and may be controlled to advance or retreat by forward and reverse rotations of the second spiral slotted disc. The second motor may be connected with a worm of the third worm-and-gear pair via a second coupler and may be configured to control the third worm-and-gear pair to move. The clamping handwheel may be connected with a worm of the first worm-and-gear pair via a flat key, and the first worm-and-gear pair may be moved by rotating the clamping handwheel; and a worm gear of the second worm-and-gear pair may be located between the first clamps and the cutters and coaxially connected to the first spiral slotted disc. The third motor may be connected with a worm of the second worm-and-gear pair via a third coupler and may be configured to control the second worm-and-gear pair to move.

In some embodiments, the pressure-retaining drill disengaging device may include an end cover, a clamping cabin, a disengaging cabin, a pressure-retaining cylinder, a worm, two clamp handles, a disengaging slide sleeve, a worm gear and second clamps. The clamping cabin may be connected with the end cover and the disengaging cabin via bolts, and the pressure-retaining cylinder may be connected with the disengaging cabin via a flange. The second clamps may be arranged in the clamp handles via bearings, the two clamp handles may be symmetrically arranged at two sides of the clamping cabin, and the second clamps may be controlled to advance or retreat by rotating the clamp handles; and the worm gear may be arranged in the disengaging cabin, the disengaging slide sleeve may be connected with the worm gear via a feather key, and the worm gear may be driven to rotate by rotating the worm to control the disengaging slide sleeve to move.

In some embodiments, the monitoring and operating system may include a control console, a display, the valve control panel, an exhaust display device, a computer host and a power distribution cabinet. The display may be configured for displaying a progress of core sample transferring and conditions of each of executing elements including rotational speeds and torques of the first motor, the second motor and the third motor, and a pressure and medium temperature curve within the transfer and online detection system; the valve control panel may be configured for controlling inflow and exhaust of the branches; and the power distribution cabinet may be configured for supplying power to the executing elements and collecting data fed back by the executing elements.

In some embodiments, the seawater cooling and pressurizing system may include the seawater booster pump, a first compressor, a first condenser, a water storage tank, a first circulating pump, a second compressor, a second evaporator, a second condenser, a second circulating pump, a first evaporator and an installation chassis. The first compressor, the first condenser, the second circulating pump and the first evaporator may jointly constitute a primary-efficiency cooling unit. The first circulating pump, the second compressor, the second evaporator and the second condenser may jointly constitute a high-efficiency cooling unit; and the seawater booster pump, the water storage tank, the primary-efficiency cooling unit and the high-efficiency cooling unit may be fixed on the installation chassis.

In some embodiments, the pressure-retaining cylinder may be provided with a pressure-retaining cylinder visible window, a pressure-retaining cylinder water inlet, a pressure-retaining cylinder drainage port, a pressure-retaining cylinder exhaust port. The clamping cabin may be provided with a clamping cabin visible window, a clamping cabin water inlet, a clamping cabin drainage port and a clamping cabin exhaust port. The subsample pressure-retaining storage cylinder may be provided with a subsample pressure-retaining storage cylinder water inlet and a subsample pressure-retaining storage cylinder exhaust port. The pressure-retaining cylinder, the clamping cabin and the subsample pressure-retaining storage cylinder each may be mounted with a pressure gage and an explosion proof valve.

The present disclosure further provides an application method of a transfer and online detection system for deep-sea sediment samples, including the following steps:

cooling seawater: filling a water storage tank with the seawater, starting up a primary-efficiency cooling unit, setting a target temperature to 8° C., shutting down a primary-efficiency cooling unit when a temperature of the seawater drops to the target temperature, starting up a high-efficiency cooling unit, and setting the target temperature to 3° C.;

installing a sampling drill: installing the sampling drill in a pressure-retaining drill disengaging device, clamping an inner barrel joint of the sampling drill by second clamps, holding tightly an inner barrel of the sampling drill by a disengaging slide sleeve, and connecting the pressure-retaining drill disengaging device with a high-pressure ball valve via a fourth hoop;

conducting exhausting and pressurizing for the transfer and online detection system: opening all water inlet ball valves and exhaust port ball valves as well as the high-pressure ball valve to ensure communication within the transfer and online detection system; starting up a seawater booster pump to inject the seawater into the transfer and online detection system, and observing a venting condition of an exhaust display device; shutting down the seawater booster pump after the seawater is discharged through an exhaust port, and starting up a pneumatic booster pump to repeatedly open and close the exhaust port ball valves multiple times until bubbles flow out; closing the exhaust port ball valves, such that a pressure within the transfer and online detection system begins to rise, observing reading on all pressure gages and shutting down the pneumatic booster pump to allow the transfer and online detection system enter a pressure maintaining state when the pressure within the transfer and online detection system pressure rise to a predetermining value;

disengaging the sampling drill from the inner barrel: rotating a worm with a worm handle to a predetermined number of turns, and observing through the visible window, whether the inner barrel joint and the inner barrel of the sampling drill are disengaged;

gripping a core: starting up a first motor to drive a gripper to move forwards so as to contact and grab the core; and reversely rotating the first motor to pull the core out of the sampling drill to a sample segment cutting device;

cutting the core: rotating a clamping handwheel on the sample segment cutting device to drive first clamps to clamp the core, then starting up a second motor and a third motor to cut the core, resetting the second motor and the third motor after cutting is finished, and reversely rotating the clamping handwheel to reset the first clamps; and subpackaging core samples: closing the high-pressure ball valve to release pressure in the disengaging device, and then detaching the pressure-retaining drill disengaging device from the transfer and online detection system; connecting a subsample pressure-retaining storage cylinder with the transfer and online detection system to exhaust and pressurize the subsample pressure-retaining storage cylinder until a balance between the pressure in the subsample pressure-retaining storage cylinder and a pressure in the transfer and online detection system is reached, and opening the high-pressure ball valve; starting up the first motor to push the core samples cut into the subsample storage pressure-retaining cylinder, and closing ball valves on the subsample pressure-retaining storage cylinder and the high-pressure ball valve on the transfer and online detection system, and detaching the subsample pressure-retaining storage cylinder from the transfer and online detection system; and installing a new subsample pressure-retaining storage cylinder, and performing a new cycle of core cutting and storage by repeated operations of exhausting and pressurizing.

The present embodiment achieves the following technical effects as compared with the prior art:

The transfer and online detection system for deep-sea sediment samples provided by the present embodiment may achieve the transferring, detecting and analyzing, segment cutting and subpackaging and storing of 3-meter core samples in an environment of high pressure and low temperature, during which pressure and temperature fluctuation within the system may be maintained at 5% or below. The system may conduct acoustic testing and CT (Computed Tomography) scanning on the core samples in addition to transferring the core samples, thereby alleviating the impact of disturbance generated in the transfer process on the detection result. The system may guarantee that pressure and temperature of the environment where the core samples are located are similar to their in-situ pressure and temperature.

BRIEF DESCRIPTION OF THE DRAWINGS

To describe the technical solutions in the embodiments of the present disclosure or in the prior art more clearly, the accompanying drawings required for the embodiments will be briefly described below. Apparently, the accompanying drawings described below are merely some embodiments of the present disclosure, and a person of ordinary skill in the art may also obtain other accompanying drawings based on these accompanying drawings without creative efforts.

Figure 1:
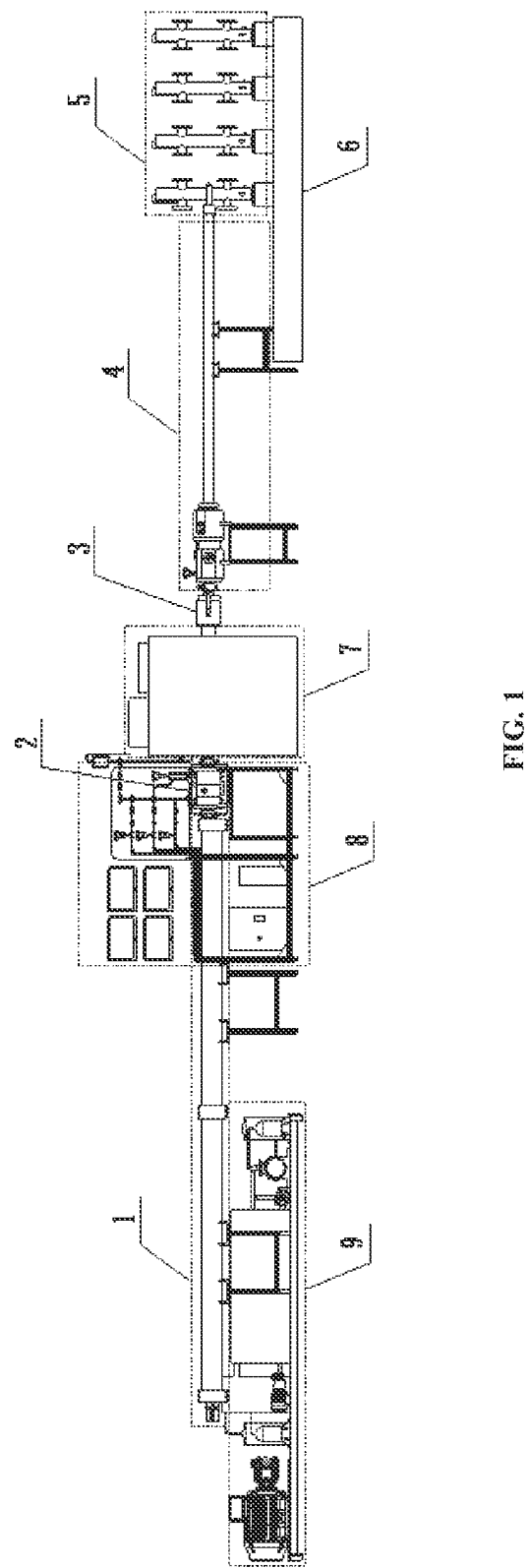
FIG. 1 is a schematic diagram of a transfer and online detection system for deep-sea sediment samples according to the present disclosure.

Reference numerals, 1 sample gripping and feeding device, 2 sample segment cutting device, 3 high-pressure ball valve, 4 pressure-retaining drill disengaging device, 5 subsample pressure-retaining storage cylinder, 6 cool water tank, 7 online sample detection device, 8 monitoring and operating system, 9 seawater cooling and pressurizing system, 101 first motor, 102 first hoop, 103 front pressure-retaining cylinder segment, 104 second hoop, 105 rear pressure-retaining cylinder segment, 106 third hoop, 107 rear end cover, 108 lead screw, 109 guide rail, 110 gripper, 111 auxiliary supporting slide block, 112 gripping rod, 113 gears joint, 114 driving slide block, 115 front end cover, 116 first auxiliary motor, 117 pinion, 118 main gear, 119 guide groove sleeve, 201 cabin, 202 right end cover, 203 second motor, 204 clamping handwheel, 205 left end cover, 206 third motor, 207 first worm-and-gear pair, 208 second worm-and-gear pair, 209 third worm-and-gear pair, 210 cutter, 211 first spiral slotted disc, 212 first clamp, 213 second spiral slotted disc, 214 cutting limiting disc, 401 end cover, 402 clamping cabin, 403 disengaging cabin, 404 pressure-retaining cylinder, 405 worm, 406 clamp handle, 407 disengaging slide sleeve, 408 worm gear, 409 second clamp, 801 control console, 802 display, 803 valve control panel, 804 exhaust display device, 805 computer host, 806 power distribution cabinet, 901 seawater booster pump, 902 first compressor, 903 first condenser, 904 water storage tank, 905 first circulating pump, 906 second compressor, 907 second evaporator, 908 second condenser, 909 second circulating pump, 910 first evaporator, 911 installation chassis, 1001 first drainage port ball valve, 1002 second drainage port ball valve, 1003 water inlet ball valve, 1004 first exhaust port ball valve, 1005 second exhaust port ball valve, 1006 third exhaust port ball valve, 1007 fourth exhaust port ball valve, 8031 water inlet main ball valve, 8032 first branch ball valve, 8033 second branch ball valve, 8034 third branch ball valve, 8035 master pressure relief ball valve, 8036 third branch pressure gage, 8037 second branch pressure gage, 8038 first branch pressure gage, and 8039 main pressure gage.

DETAILED DESCRIPTION OF THE EMBODIMENTS

The technical solutions of the embodiments of the present disclosure are clearly and completely described below with reference to the accompanying drawings of the embodiments. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

The objective of the present embodiment is to provide a transfer and online detection system for deep-sea sediment samples and an application method thereof to resolve the foregoing problems in the prior art, so that acquired samples may be cut into random segments while the in-situ pressure is maintained and are stored and conveyed to a laboratory under retained pressure to better study physical properties of sediments.

To make the above-mentioned objectives, features, and advantages of the present disclosure clearer and more comprehensible, the present disclosure will be further described in detail below with reference to the accompanying drawings and the specific implementation.

The present disclosure provides a transfer and online detection system for deep-sea sediment samples, which includes, as shown in FIGS. 1 to 9, a sample gripping and feeding device 1, a sample segment cutting device 2, a high-pressure ball valve 3, a pressure-retaining drill disengaging device 4, a subsample pressure-retaining storage cylinder 5, a cool water tank 6, a sample online detection device 7, a monitoring and operating system 8, and a seawater cooling and pressurizing system 9. The sample gripping and feeding device 1, the sample segment cutting device 2, the online sample detection device 7, the high-pressure ball valve 3, and the pressure-retaining drill disengaging device 4 are coaxially connected together in sequence. The coaxial connection between the sample gripping and feeding device 1 and the sample segment cutting device 2, the coaxial connection between the sample segment cutting device 2 and the online sample detection device 7, and the coaxial connection between the high-pressure ball valve 3 and the pressure-retaining drill disengaging device 4 are implemented via hoops respectively. The coaxial connection between the online sample detection device 7 and the high-pressure ball valve 3 is implemented via a flange. A seawater booster pump 901 in the seawater cooling and pressurizing system 9 is connected with a water inlet main ball valve 8031 in a valve control panel 803 through a pipeline, and the valve control panel 803 is connected with the sample gripping and feeding device 1, the sample segment cutting device 2, the high-pressure ball valve 3 and the pressure-retaining drill disengaging device 4 through pipelines.

Figure 2:
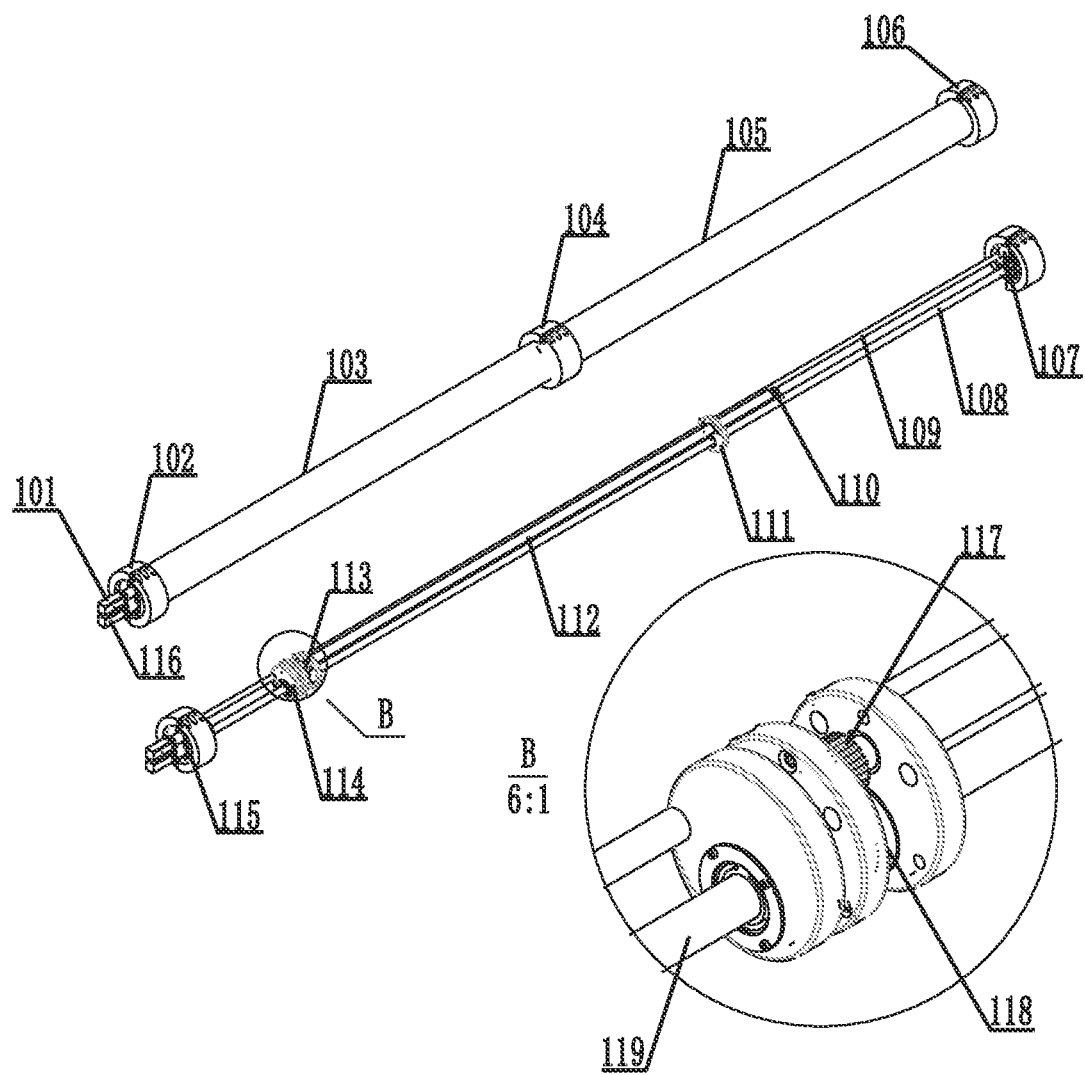
FIG. 2 is a schematic diagram of a sample gripping and feeding device according to the present disclosure.

As shown in FIG. 2, the sample gripping and feeding device 1 of the transfer and online detection system for deep-sea sediment samples in the present disclosure includes a first motor 101, a first hoop 102, a front pressure-retaining cylinder segment 103, a second hoop 104, a rear pressure-retaining cylinder segment 105, a third hoop 106, a rear end cover 107, a lead screw 108, a guide rail 109, a gripper 110, an auxiliary supporting slide block 111, a gripping rod 112, a gears joint 113, a driving slide block 114 and a front end cover 115. The front pressure-retaining cylinder segment 103 and the front end cover 115 are coaxially connected via the first hoop 102, the front pressure-retaining cylinder segment 103 and the rear pressure-retaining cylinder segment 105 are coaxially connected via the second hoop 104, and the rear pressure-retaining cylinder segment 105 and the rear end cover 107 are coaxially connected via the third hoop 106. The guide rail 109 is arranged on the front pressure-retaining cylinder segment 103 and the rear pressure-retaining cylinder segment 105 via screws and plays a guiding role in axial movement of the auxiliary supporting slide block and the driving slide block. The auxiliary supporting slide block and the driving slide block each are arranged on the guide rail 109 and coaxial with the front pressure-retaining cylinder segment 103 and form gaps between the auxiliary supporting slide block and the driving slide block and the inner wall of the front pressure-retaining cylinder segment 103. Two ends of the lead screw 108 are arranged on the front end cover 115 and the rear end cover 107 respectively, and the lead screw 108 penetrates through the through holes in the driving slide block 114 and the auxiliary supporting slide block 111. The gears joint 113 is arranged on the lead screw 108, one end of the gripping rod 112 is fixedly connected with the gears joint 113, and the other end of the gripping rod 112 is provided with the gripper 111. The gears joint 113 can convert rotational movement of the lead screw 108 into axial translational movement of the gripping rod 112. The driving slide block and nut of the lead screw 108 are connected via a flange bearing. The gears joint 113 is divided into a main gear 118 and a pinion 117. The nut of the lead screw 108 is connected with the main gear 118 via a key. The gripping rod 112 is fixedly connected with the pinion 117 and is connected with the driving slide block via a flange bearing. When the first motor works alone, the lead screw 108 rotates, and the driving slide block, the gears joint 113, and the gripping rod 112 move in translation together with the nut of the lead screw. When the first motor and a first auxiliary motor 116 work at the same time, the lead screw and a guide groove sleeve 119 are rotated simultaneously, the nut of the lead screw has movements of translation and rotation at the same time, the driving slide block only translates, the main gear 118 translates and rotates with the nut, and the pinion 117 drives the gripping rod 112 to translate and rotate. The first motor 101 is connected with one end of the lead screw 108 via a coupler and is configured to drive the lead screw 108 to rotate.

Figure 3:
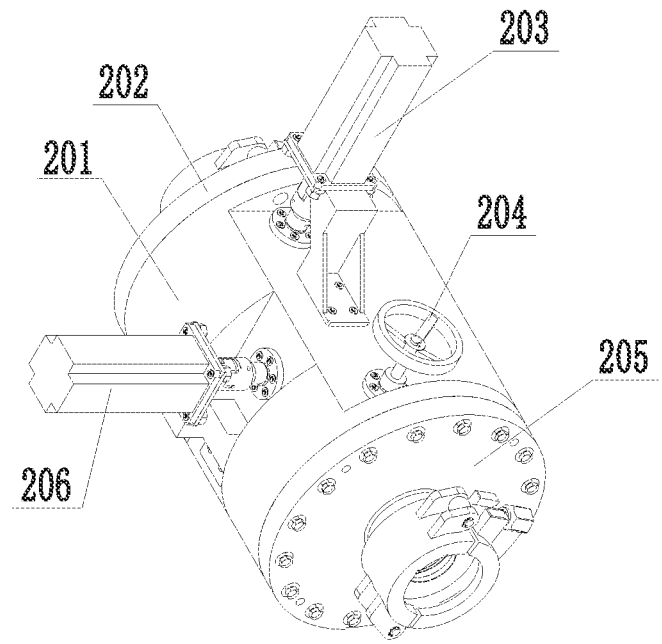
FIG. 3 is a schematic diagram of a sample segment cutting device according to the present disclosure.
Figure 4:
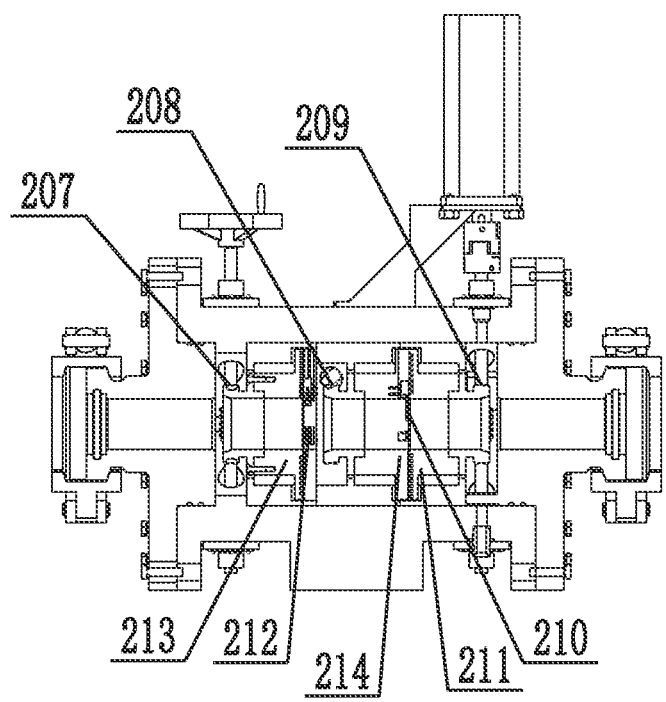
FIG. 4 is a sectional diagram of the sample segment cutting device according to the present disclosure.

As shown in FIGS. 3 and 4, the sample segment cutting device 2 of the transfer and online detection system for deep-sea sediment samples in the present disclosure includes a cabin 201, a right end cover 202, a second motor 203, a clamping handwheel 204, a left end cover 205, a third motor 206, a first worm-and-gear pair 207, a second worm-and-gear pair 208, a third worm-and-gear pair 209, cutters 210, a first spiral slotted disc 211, first clamps 212 and a second spiral slotted disc 213. The right end cover 202, the left end cover 205 and the cabin 201 are all coaxially connected via bolts. A worm gear of the first worm-and-gear pair 207, a worm gear of the third worm-and-gear pair 209, the first spiral slotted disc 211 and the second spiral slotted disc 213 are all coaxially arranged in the cabin 201. The worm gear of the first worm-and-gear pair 207 and the second spiral slotted disc 213 are coaxially connected via bolts, and the worm gear of the third worm-and-gear pair 209 and the first spiral slotted disc 211 are coaxially connected via bolts. The three cutters 210 are arranged on the first spiral slotted disc 211 at an interval of 120 degrees and are controlled to advance or retreat by the forward and reverse rotation of the first spiral slotted disc 211. The three first clamps 212 are arranged on the second spiral slotted disc 213 at an interval of 120 degrees and are controlled to advance or retreat by the forward and reverse rotation of the second spiral slotted disc 213. The second motor 203 is connected with a worm of the third worm-and-gear pair 209 via a coupler and is configured to control the third worm-and-gear pair 209 to move. The clamping handwheel 204 is connected with a worm of the first worm-and-gear pair 207 via a flat key. The movement of the first worm-and-gear pair 207 is controlled by rotating the clamping handwheel 204. The third motor 206 is connected with a worm of the second worm-and-gear pair 208 via a coupler and is configured to control the second worm-and-gear pair 208 to move. A worm gear of the second worm-and-gear pair 208 is fixedly connected to a cutting limiting disc 214. The difference in rotational speed between the cutting limiting disc 214 and the first spiral slotted disc 211 is used to realize the rotation of the cutters 210 while advancing.

Figure 5:
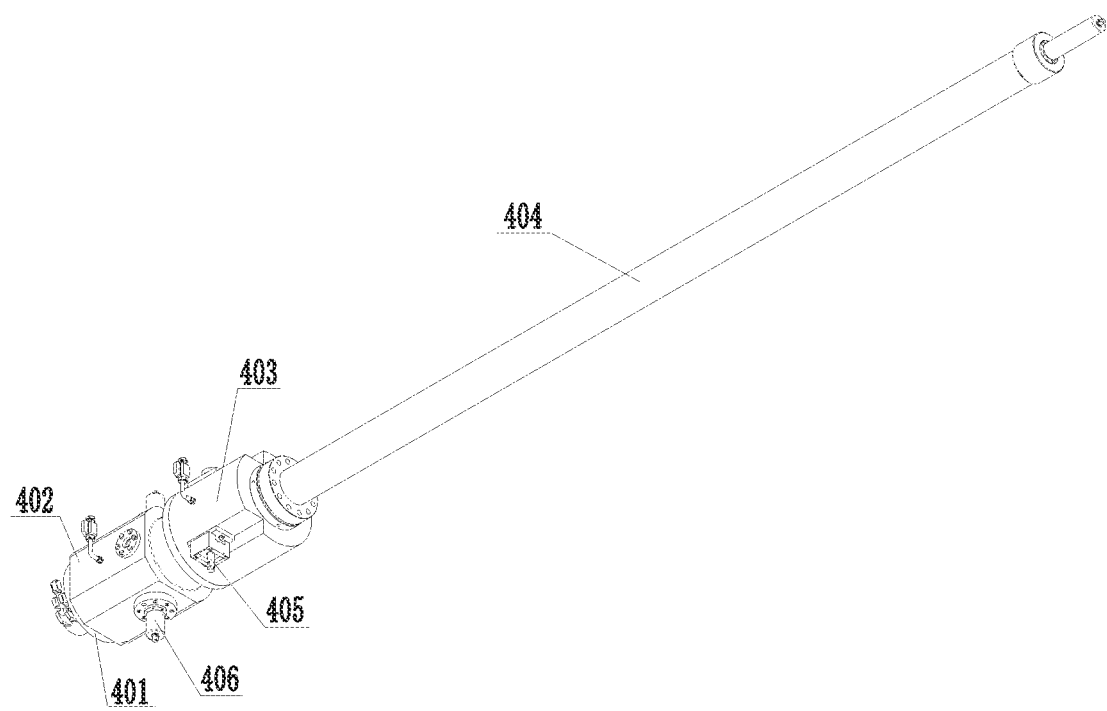
FIG. 5 is a schematic diagram of a pressure-retaining drill disengaging device according to the present disclosure.
Figure 6:
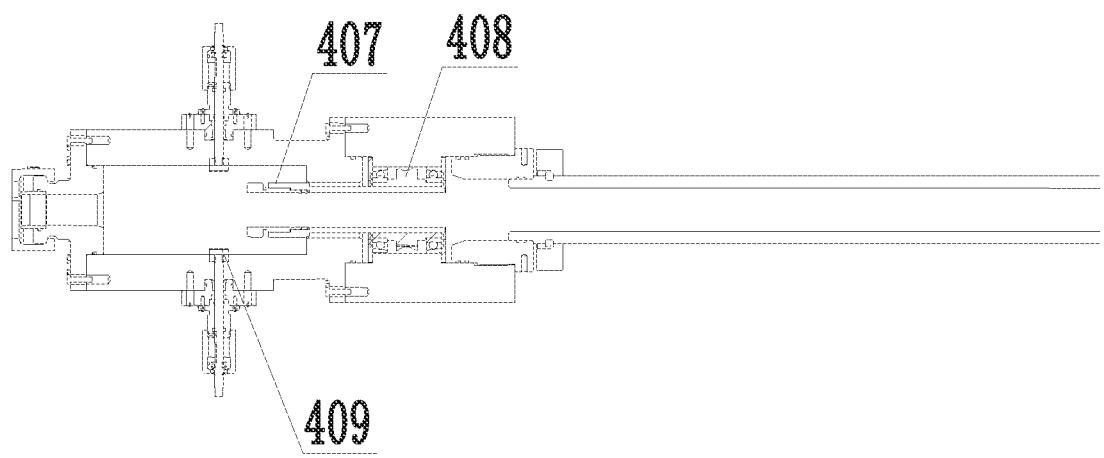
FIG. 6 is a sectional diagram of the pressure-retaining drill disengaging device according to the present disclosure.

As shown in FIGS. 5 and 6, the pressure-retaining drill disengaging device of the transfer and online detection system for deep-sea sediment samples in the present disclosure includes an end cover 401, a clamping cabin 402, a disengaging cabin 403, a pressure-retaining cylinder 404, a worm 405, clamp handles 406, a disengaging slide sleeve 407, a worm gear 408 and second clamps 409. The clamping cabin 402 is connected with both the end cover 401 and the disengaging cabin 403 via bolts, and the pressure-retaining cylinder 404 is connected with the disengaging cabin 403 via a flange. The second clamps 409 are arranged in the clamp handles 406 via bearings respectively. The two clamp handles 406 are symmetrically arranged at two sides of the clamping cabin 402, and the clamps 409 are controlled to advance or retreat by rotating the clamp handles 406 respectively. The worm gear 408 is arranged in the disengaging cabin 403, the disengaging slide sleeve 407 is connected with the worm gear 408 via a feather key, and the worm gear 408 is driven to rotate by the rotation of the worm 405 to control the disengaging slide sleeve 407 to move. The pressure-retaining drill disengaging device has a function of the unscrewing the threaded connection between the inner barrel joint and the inner barrel of the drill under high pressure. The inner barrel joint is clamped by the second clamps 409, the inner barrel is clamped by the disengaging slide sleeve with the expansion sleeve, the worm gear 408 drives the disengaging slide sleeve and the inner barrel to rotate, and the threaded connection is unscrewed. The disengaging slide sleeve and the inner barrel are moved backwards by the force of the thread.

Figure 7:
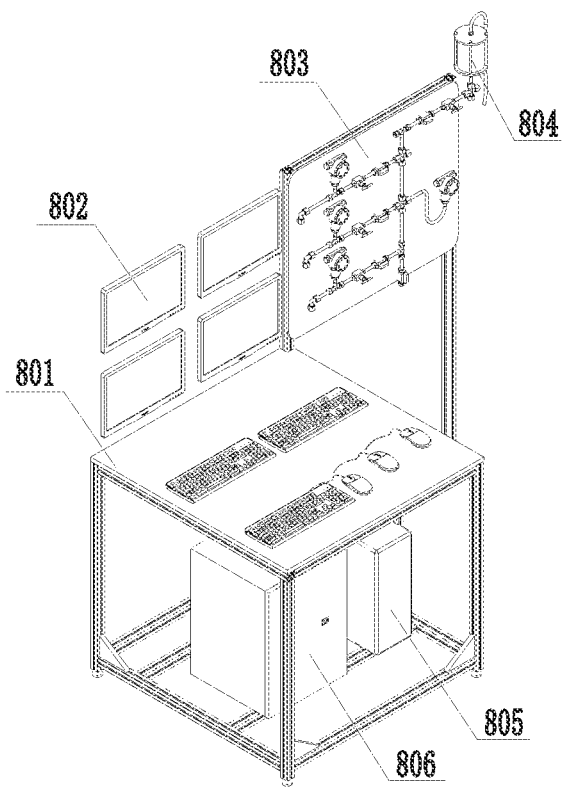
FIG. 7 is a schematic diagram of a monitoring and operating system according to the present disclosure.

As shown in FIG. 7, the monitoring and operating system of the transfer and online detection system for deep-sea sediment samples in the present disclosure includes a control console 801, a display 802, a valve control panel 803, an exhaust display device 804, a computer host 805 and a power distribution box 806. The display 802 is configured for displaying a progress of core transferring and conditions of each of the executing elements (such as the first motor, the first auxiliary motor, the second motor and the third motor) including the rotational speeds and torques of the first motor 101, the second motor 203 and the third motor 206, and a pressure and medium temperature curve within the transfer and online detection system. The valve control panel 803 is configured for controlling inflow and exhaust of each branch; and the power distribution box 806 is configured for supplying power to each executing element and collecting data fed back by each executing element.

Figure 8:
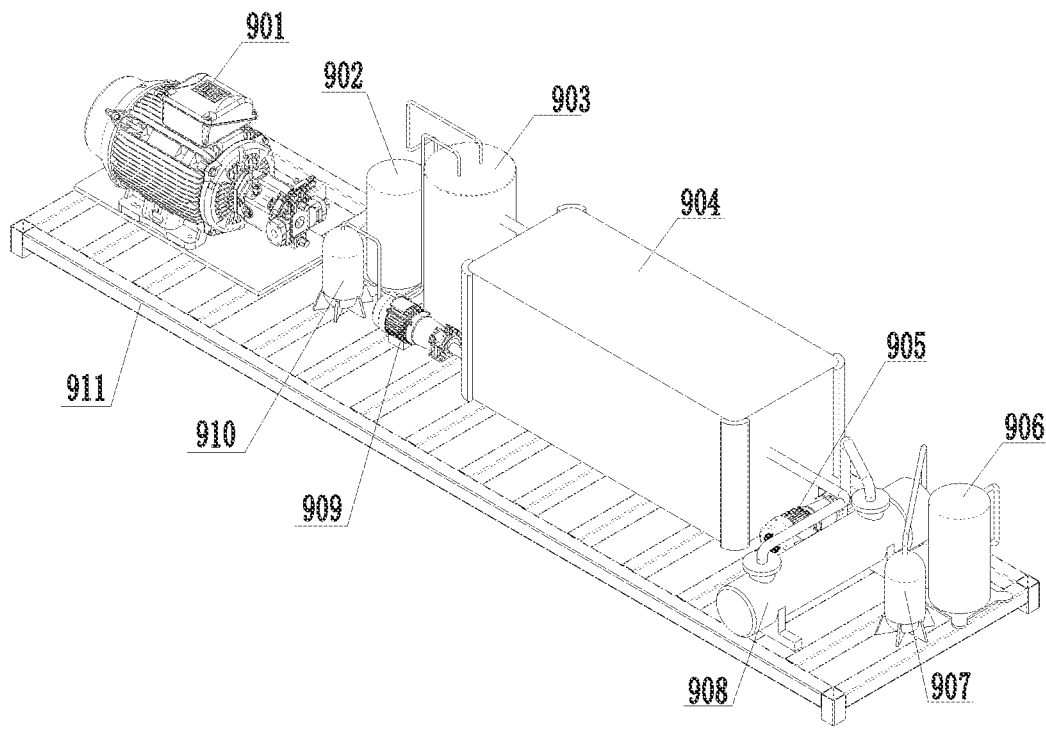
FIG. 8 is a schematic diagram of a seawater cooling and pressurizing system according to the present disclosure.
Figure 9:
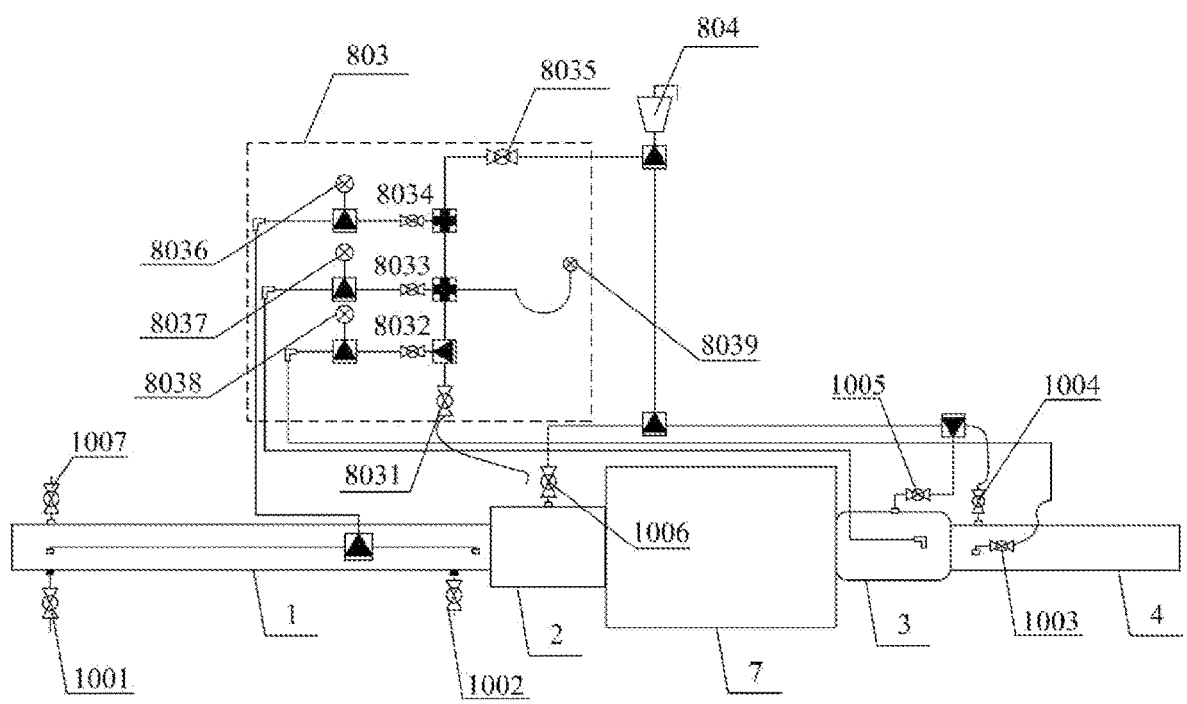
FIG. 9 is a connection diagram of a valve control panel and a pressure-retaining transfer device according to the present disclosure.

As shown in FIG. 8, the seawater cooling and pressurizing system 9 of the transfer and online detection system for deep-sea sediment samples in the present disclosure includes a seawater booster pump 901, a first compressor 902, a first condenser 903, a water storage tank 904, a first circulating pump 905, a second compressor 906, a second evaporator 907, a second condenser 908, a second circulating pump 909, a first evaporator 910 and an installation chassis 911. The first compressor 902, the first condenser 903, the second circulating pump 909 and the first evaporator 910 jointly constitute a primary-efficiency cooling unit capable of cooling seawater at normal temperature to around 10° C. The first circulating pump 905, the second compressor 906, the second evaporator 907 and the second condenser 908 jointly constitute a high-efficiency cooling unit capable of cooling seawater at 10° C. to around 2° C. The seawater booster pump 901, the water storage tank 904, the primary-efficiency cooling unit and the high-efficiency cooling unit are all fixed onto the installation chassis 911. One end of a water inlet main ball valve 8031 is connected with the seawater booster pump 901, and the other end of the water inlet main ball valve is separately connected with a first branch ball valve 8032, a second branch ball valve 8033, and a third branch ball valve 8034 via a main path. The first branch ball valve 8032, the second branch ball valve 8033, and the third branch ball valve 8034 are connected with the pressure-retaining drill disengaging device 4, the high-pressure ball valve 3 and the sample gripping and feeding device 1 respectively. A first exhaust port ball valve 1004, a second exhaust port ball valve 1005, a third exhaust port ball valve 1006 and a fourth exhaust port ball valve 1007 are connected to the pressure-retaining drill disengaging device 4, the high-pressure ball valve 3, the sample segment cutting device 2 and the sample gripping and feeding device 1 respectively, and are connected with the exhaust display device 804 through pipelines, the exhaust display device 804 is connected with the main path through a pipeline provided with the master pressure relief ball valve 8035, and the first drainage port ball valve 1001 and the second drainage port ball valve 1002 are arranged on the sample gripping and feeding device 1; and the main path pressure gage 8039 is connected to the main path, and the first branch pressure gage 8038, the second branch pressure gage 8037, and the third branch pressure gage 8036 are connected to branch paths where the first branch ball valve 8032, the second branch ball valve 8033, and the third branch ball valve 8034 are located.

A working method of the transfer and online detection system for deep-sea sediment samples includes the following steps:

Step 1: cooling seawater. Step 1 specifically includes the sub steps of filling the water storage tank 904 with the seawater, switching on the system power supply, starting up the primary-efficiency cooling unit, setting a target temperature to 8° C., shutting down the primary-efficiency cooling unit when a water temperature of the seawater drops to 8° C., starting up the high-efficiency cooling unit, setting the target temperature to 3° C., and shutting down the high-efficiency cooling unit when the water temperature drops to 3° C.

Step 2: installing the sampling drill. Step 2 specifically includes the sub steps of firstly putting the sampling drill into the cool water tank 6 for primary cooling after the sampling drill is lifted onto a deck from the seabed, installing the sampling drill into the pressure-retaining drill disengaging device 4 after finishing the cooling of the sampling drill, so that the second clamps 409 clamp the inner barrel joint of the sampling drill, and the disengaging slide sleeve 407 supports tightly the inner barrel of the sampling drill, connecting the pressure-retaining drill disengaging device 4 with the high-pressure ball valve 3 via the hoop, and ensuring that the water inlet ball valve 1003 and the exhaust port ball valve 1004 on the pressure-retaining drill disengaging device 4 are connected to corresponding branches on the valve control panel 803 through pipelines.

Step 3: conducting exhausting and pressurizing for the transfer and online detection system. Step 3 specifically includes the substeps of communicating the interior across the entire transfer and online detection system by way of opening the water inlet main ball valve 8031, the first branch ball valve 8032, the second branch ball valve 8033 and the third branch ball valve 8034, opening the water inlet ball valve 1003, opening the first exhaust port ball valve 1004, the second exhaust port ball valve 1005, the third exhaust port ball valve 1006 and the fourth exhaust port ball valve 1007, closing the first drainage port ball valve 1001 and the second drainage port ball valve 1002, closing the master pressure relief ball valve 8035, and opening the high-pressure ball valve; starting up the seawater booster pump 901 to inject seawater into the transfer and online detection system, and observing the venting condition in the exhaust display device 804; shutting down the seawater booster pump 901 after the exhaust display device 804 starts to discharge water, and starting up the pneumatic booster pump, and repeatedly opening and closing the first exhaust port ball valve 1004, the second exhaust port ball valve 1005, the third exhaust port ball valve 1006 and the fourth exhaust port ball valve 1007 multiple times until there are few bubbles flowing out of the exhaust display device 804; closing the first exhaust port ball valve 1004, the second exhaust port ball valve 1005, the third exhaust port ball valve 1006 and the fourth exhaust port ball valve 1007, and observing the reading on the third branch pressure gage 8036, second branch pressure gage 8037, first branch pressure gage 8038 and main pressure gage 8039 when the pressure within the transfer and online detection system begins to rise; and shutting down the pneumatic booster pump when the pressure within the transfer and online detection system rises to a MPa to enable the pressure within the transfer and online detection system to enter a pressure-maintaining state, where the value of a is determined in accordance with the sampling depth.

Step 4: conducting barrel removal on the sampling drill. Step 4 specifically includes the substeps of rotating the worm 405 by a certain number of turns, and observing through the visible window whether threaded connection s between the inner barrel joint and the inner barrel of the sampling drill are disengaged; and reversely rotating the clamp handles 406 to retreat the clamp 409 so that the inner barrel joint of the sampling drill can fall onto the bottom of the clamping cabin 402;

Step 5: gripping the core. Step 5 specifically includes the substeps of starting up the first motor 101 to drive the lead screw 108 to rotate, so as to move the gripper 110 forwards under the drive of the lead screw 108 through the sample gripping and feeding device 1, the sample segment cutting device 2, the high-pressure ball valve 3 and the sample online detection device 7 in sequence to enter the pressure-retaining drill disengaging device 4, and continuing to move the gripper forwards for a distance b after the gripper is in contact with sample barrels before its stop, where b accounts for ⅔ of the length of the gripper in mm; and reversely rotating the first motor 101 to pull the core out of the sampling drill into the sample segment cutting device 2, and starting up the online sample detection device 7 in the process to detect the core;

Step 6: cutting the core. Step 6 specifically includes the sub steps of moving the core to space the tail end of the core apart from the cutters 210 by a distance d mm, where the value of d is determined according to actual demands; rotating the clamping handwheel 204 for a certain number of turns to drive the first clamps 212 to clamp the core, starting up the second motor 203 and the third motor 206, to drive the cutters 210 to cut the core, where the amount of feeding is controlled by setting the number of turns for which the second motor 203 and the third motor 206 rotate; and resetting the second motor 203 and the third motor 206 after cutting is finished, retreating the cutters 210, and reversely rotating the clamping handwheel 204 to retreat the first clamps 212;

Step 7: subpackaging the core samples. Step 7 specifically includes the substeps of closing the high-pressure ball valve 3 to release the pressure in the pressure-retaining drill disengaging device 4, and then detaching the pressure-retaining drill disengaging device 4 from the transfer and online detection system; connecting the subsample pressure-retaining storage cylinder 5 with the high-pressure ball valve 3 via the hoop to exhaust and pressurize the subsample pressure-retaining storage cylinder 5, and opening the high-pressure ball valve 3 until a balance is reached between the pressure in the subsample pressure-retaining storage cylinder and that in the transfer and online detection system; starting up the first motor 101 to push the cut core samples into the subsample pressure-retaining storage cylinder 5, and closing the high-pressure ball valve 3, and detaching the subsample pressure-retaining storage cylinder 5 from the transfer and online detection system; and installing a new sample storage cylinder, and performing a new cycle of core cutting and storage with repeated operations such as exhausting and pressurizing.

Specific examples are used for illustration of the principles and implementations of the present disclosure. The description of the embodiments is used to help understand the method and its core ideas of the present disclosure. In addition, persons of ordinary skill in the art can make various modifications in terms of specific implementations and scope of application according to the teachings of the present disclosure. In conclusion, the content of the present specification should not be construed as a limitation to the present disclosure.

What is claimed is:

1. A transfer and online detection system for deep-sea sediment samples, comprising a sample gripping and feeding device, a sample segment cutting device, a ball valve, a pressure-retaining drill disengaging device, a subsample pressure-retaining storage cylinder, a cool water tank, an online sample detection device, a monitoring and operating system, and a seawater cooling and pressurizing system, wherein the sample gripping and feeding device, the sample segment cutting device, the online sample detection device, the ball valve and the pressure-retaining drill disengaging device are coaxially connected together in sequence; a seawater booster pump in the seawater cooling and pressurizing system is connected with a water inlet main ball valve in a valve control panel through a pipeline, and the valve control panel is connected with the sample gripping and feeding device, the sample segment cutting device, the ball valve and the pressure-retaining drill disengaging device through branches and valves on the branches; and the cool water tank is configured for cooling a sampling drill, the pressure-retaining drill disengaging device is configured for disengaging an inner barrel from an inner barrel joint of the sampling drill, and the sample gripping and feeding device and the sample segment cutting device are configured for gripping and cutting core samples, and conveying the core samples cut into the subsample pressure-retaining storage cylinder for storage;

wherein the sample gripping and feeding device comprises a first motor, a first hoop, a front pressure-retaining cylinder segment, a second hoop, a rear pressure-retaining cylinder segment, a third hoop, a rear end cover, a lead screw, a guide rail, a gripper, an auxiliary supporting slide block, a gripping rod, a gears joint, a driving slide block and a front end cover, wherein the front pressure-retaining cylinder segment and the front end cover are coaxially connected via the first hoop, the front pressure-retaining cylinder segment and the rear pressure-retaining cylinder segment are coaxially connected via the second hoop, and the rear pressure-retaining cylinder segment and the rear end cover are coaxially connected via the third hoop; the guide rail is arranged in the front pressure-retaining cylinder segment and the rear pressure-retaining cylinder segment via screws, and configured for guiding the auxiliary supporting slide block and the driving slide block to axially move; the auxiliary supporting slide block and the driving slide block each are arranged on the guide rail and coaxial with the front pressure-retaining cylinder segment, and form a gap with an inner wall of the front pressure-retaining cylinder segment; two ends of the lead screw are arranged to the front end cover and the rear end cover respectively, the lead screw penetrates through through holes in the driving slide block and the auxiliary supporting slide block, the gears joint is arranged on the lead screw, one end of the gripping rod is fixedly connected with the gears joint, another end of the gripping rod is provided with the gripper, and the gears joint is capable of converting rotational movement of the lead screw into axial translational movement of the gripping rod; and the first motor is connected with one end of the lead screw via a first coupler, and is configured to drive the lead screw to rotate; and wherein the sample segment cutting device comprises a cabin, a right end cover, a second motor, a clamping handwheel, a left end cover, a third motor, a first worm-and-gear pair, a second worm-and-gear pair, a third worm-and-gear pair, three cutters, a first spiral slotted disc, three first clamps and a second spiral slotted disc; wherein the right end cover and the left end cover are coaxially connected to the cabin via bolts; a worm gear of the first worm-and-gear pair, a worm gear of the third worm-and-gear pair, the first spiral slotted disc and the second spiral slotted disc are coaxially arranged in the cabin, the worm gear of the first worm-and-gear pair are coaxially connected to the second spiral slotted disc via bolts, and the worm gear of the third worm-and-gear pair are coaxially connected to the first spiral slotted disc via bolts; the three cutters are arranged on the first spiral slotted disc at an interval of 120 degrees, and are controlled to advance or retreat by forward and reverse rotations of the first spiral slotted disc; the first clamps are arranged on the second spiral slotted disc at an interval of 120 degrees, and are controlled to advance or retreat by forward and reverse rotations of the second spiral slotted disc; the second motor is connected with a worm of the third worm-and-gear pair via a second coupler, and is configured to control the third worm-and-gear pair to move; the clamping handwheel is connected with a worm of the first worm-and-gear pair via a flat key, and the first worm-and-gear pair is moved by rotating the clamping handwheel; and a worm gear of the second worm-and-gear pair is located between the first clamps and the cutters, and coaxially connected to the first spiral slotted disc; the third motor is connected with a worm of the second worm-and-gear pair via a third coupler, and is configured to control the second worm-and-gear pair to move.

2. The transfer and online detection system according to claim 1, wherein the pressure-retaining drill disengaging device comprises an end cover, a clamping cabin, a disengaging cabin, a pressure-retaining cylinder, a worm, two clamp handles, a disengaging slide sleeve, a worm gear and second clamps; wherein the clamping cabin is connected with the end cover and the disengaging cabin via bolts, and the pressure-retaining cylinder is connected with the disengaging cabin via a flange; the second clamps are arranged in the clamp handles via bearings, the two clamp handles are symmetrically arranged at two sides of the clamping cabin, and the second clamps are controlled to advance or retreat by rotating the clamp handles; and the worm gear is arranged in the disengaging cabin, the disengaging slide sleeve is connected with the worm gear via a feather key, and the worm gear is driven to rotate by rotating the worm to control the disengaging slide sleeve to move.

3. The transfer and online detection system according to claim 2, wherein the monitoring and operating system comprises a control console, a display, the valve control panel, an exhaust display device, a computer host and a power distribution cabinet;

wherein the display is configured for displaying a progress of core sample transferring and conditions of each of executing elements including rotational speeds and torques of the first motor, the second motor and the third motor, and a pressure and medium temperature curve within the transfer and online detection system; the valve control panel is configured for controlling inflow and exhaust of the branches; and the power distribution cabinet is configured for supplying power to the executing elements and collecting data fed back by the executing elements.

4. The transfer and online detection system according to claim 3, wherein the seawater cooling and pressurizing system comprises the seawater booster pump, a first compressor, a first condenser, a water storage tank, a first circulating pump, a second compressor, a second evaporator, a second condenser, a second circulating pump, a first evaporator and an installation chassis; wherein the first compressor, the first condenser, the second circulating pump and the first evaporator jointly constitute a primary-efficiency cooling unit; the first circulating pump, the second compressor, the second evaporator and the second condenser jointly constitute a cooling unit; and the seawater booster pump, the water storage tank, the primary-efficiency cooling unit and the cooling unit are fixed on the installation chassis.

5. The transfer and online detection system according to claim 4, wherein the pressure-retaining cylinder is provided with a pressure-retaining cylinder visible window, a pressure-retaining cylinder water inlet, a pressure-retaining cylinder drainage port, a pressure-retaining cylinder exhaust port; the clamping cabin is provided with a clamping cabin visible window, a clamping cabin water inlet, a clamping cabin drainage port and a clamping cabin exhaust port; the subsample pressure-retaining storage cylinder is provided with a subsample pressure-retaining storage cylinder water inlet and a subsample pressure-retaining storage cylinder exhaust port; and the pressure-retaining cylinder, the clamping cabin and the subsample pressure-retaining storage cylinder each are mounted with a pressure gage and an explosion proof valve.

6. An application method of a transfer and online detection system for deep-sea sediment samples, comprising the following steps:

cooling seawater: filling a water storage tank with the seawater, starting up a primary-efficiency cooling unit, setting a target temperature to 8° C., shutting down a primary-efficiency cooling unit when a temperature of the seawater drops to the target temperature, starting up a cooling unit, and setting the target temperature to 3° C.;

installing a sampling drill: installing the sampling drill in a pressure-retaining drill disengaging device, clamping an inner barrel joint of the sampling drill by second clamps, holding tightly an inner barrel of the sampling drill by a disengaging slide sleeve, and connecting the pressure-retaining drill disengaging device with a ball valve via a fourth hoop;

conducting exhausting and pressurizing for the transfer and online detection system:

opening all water inlet ball valves and exhaust port ball valves as well as the ball valve to ensure communication within the transfer and online detection system; starting up a seawater booster pump to inject the seawater into the transfer and online detection system, and observing a venting condition of an exhaust display device;

shutting down the seawater booster pump after the seawater is discharged through all exhaust ports, and starting up a pneumatic booster pump to repeatedly open and close the exhaust port ball valves multiple times until bubbles flow out; closing the exhaust port ball valves, such that a pressure within the transfer and online detection system begins to rise, observing reading on all pressure gages and shutting down the pneumatic booster pump to allow the transfer and online detection system enter a pressure maintaining state when the pressure within the transfer and online detection system pressure rise to a predetermining value;

disengaging the sampling drill from the inner barrel: rotating a worm with a worm handle to a predetermined number of turns, and observing through the visible window, whether the inner barrel joint and the inner barrel of the sampling drill are disengaged;

gripping a core: starting up a first motor to drive a gripper to move forwards so as to contact and grab the core; and reversely rotating the first motor to pull the core out of the sampling drill to a sample segment cutting device;

cutting the core: rotating a clamping handwheel on the sample segment cutting device to drive first clamps to clamp the core, then starting up a second motor and a third motor to cut the core, resetting the second motor and the third motor after cutting is finished, and reversely rotating the clamping handwheel to reset the first clamps; and subpackaging core samples: closing the ball valve to release pressure in the disengaging device, and then detaching the pressure-retaining drill disengaging device from the transfer and online detection system; connecting a subsample pressure-retaining storage cylinder with the transfer and online detection system to exhaust and pressurize the subsample pressure-retaining storage cylinder until a balance between the pressure in the subsample pressure-retaining storage cylinder and a pressure in the transfer and online detection system is reached, and opening the ball valve; starting up the first motor to push the core samples cut into the subsample storage pressure-retaining cylinder, and closing ball valves on the subsample pressure-retaining storage cylinder and the ball valve on the transfer and online detection system, and detaching the subsample pressure-retaining storage cylinder from the transfer and online detection system; and installing a new subsample pressure-retaining storage cylinder, and performing a new cycle of core cutting and storage by repeated operations of exhausting and pressurizing.

\* \* \* \* \*